(12) United States Patent
Sigurdsson et al.

(10) Patent No.: US 9,795,148 B2
(45) Date of Patent: Oct. 24, 2017

(54) MEAT INSPECTION SYSTEM

(71) Applicant: Marel Iceland Ehf, Gardabaer (IS)

(72) Inventors: Árni Sigurdsson, Mosfellsbae (IS); Hrafnkell Eiriksson, Kopavogur (IS)

(73) Assignee: MAREL ICELAND EHF, Gardabaer (IS)

( * ) Notice: Subject to any disclaimer, the term of this patent is extended or adjusted under 35 U.S.C. 154(b) by 7 days.

(21) Appl. No.: 15/081,183

(22) Filed: Mar. 25, 2016

(65) Prior Publication Data

US 2016/0205955 A1 Jul. 21, 2016

Related U.S. Application Data

(63) Continuation of application No. 14/799,707, filed on Jul. 15, 2015, now Pat. No. 9,307,774, which is a (Continued)

(30) Foreign Application Priority Data

Aug. 12, 2011 (DK) ................................ 2011 00607

(51) Int. Cl.
*A22C 17/00* (2006.01)
*G01N 23/12* (2006.01)
(Continued)

(52) U.S. Cl.
CPC ......... *A22C 17/008* (2013.01); *G01N 23/083* (2013.01); *G01N 23/12* (2013.01); *G01N 33/12* (2013.01)

(58) Field of Classification Search
CPC ..... A22C 21/0092; A22C 17/12; A22C 25/17; A22B 5/166
(Continued)

(56) References Cited

U.S. PATENT DOCUMENTS 5,133,687 A 7/1992 Malloy
5,150,016 A 9/1992 Sawase et al.
(Continued)

FOREIGN PATENT DOCUMENTS

EP 1889542 A1 2/2008
FR 2718612 A1 10/1995
(Continued)

OTHER PUBLICATIONS

PCT International Search Report; International Application No. PCT/EP2012/003456; Applicant: Marel Iceland Ehf; Date of Actual Completion of International Search: Oct. 23, 2012; dated Oct. 31, 2012.
(Continued)

*Primary Examiner* — Richard Price, Jr.
(74) *Attorney, Agent, or Firm* — Workman Nydegger

(57) ABSTRACT

A meat inspection and sorting line comprising supply means, a radiation inspection facility, a cutting facility and a reject facility. Meat parts are brought together and fed into the radiation inspection facility by means of a conveyor in a layer of meat parts. An undesired object is detected by the radiation inspection facility by means of e.g. an X-ray technique and a part of the layer of meat parts containing the undesired object is identified and separated from the layer of meat parts by the cutting facility. The identified and separated part of the layer of meat parts containing the undesired object is rejected by the reject facility from the layer of meat parts.

21 Claims, 6 Drawing Sheets

Figure 1:
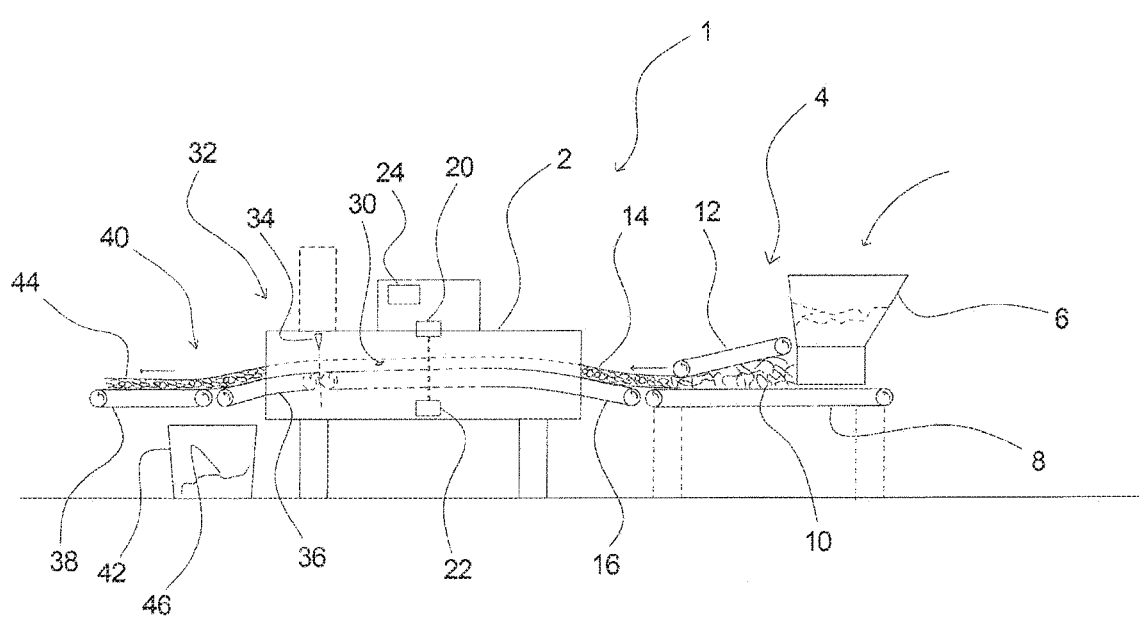

Related U.S. Application Data continuation of application No. 14/233,955, filed as application No. PCT/EP2012/003456 on Aug. 13, 2012, now Pat. No. 9,095,146.

(60) Provisional application No. 61/522,867, filed on Aug. 12, 2011.

(51) Int. Cl.
*G01N 33/12* (2006.01)
*G01N 23/083* (2006.01)

(58) Field of Classification Search
USPC .......................................... 452/125, 127–130
See application file for complete search history.

(56) References Cited

U.S. PATENT DOCUMENTS

| | | | |
|---|---|---|---|
| 5,162,016 A | 11/1992 | Malloy | |
| 5,205,779 A | 4/1993 | O'Brien et al. | |
| 5,314,375 A | 5/1994 | O'Brien et al. | |
| RE36,664 E | 4/2000 | O'Brien et al. | |
| 6,563,904 B2* | 5/2003 | Wijts | A22B 5/00 378/54 |
| 7,153,203 B2 | 12/2006 | Pfarr et al. | |
| 7,251,537 B1* | 7/2007 | Blaine | A22C 17/0086 452/156 |
| 7,452,266 B2* | 11/2008 | Bottemiller | A22C 7/00 452/150 |
| 7,651,388 B2 | 1/2010 | Faires et al. | |
| 7,841,264 B2* | 11/2010 | Kim | B26D 3/10 452/156 |
| 7,918,718 B2* | 4/2011 | Christensen | A22B 5/007 452/157 |
| 7,949,414 B2* | 5/2011 | Blaine | B26D 3/10 198/341.04 |
| 7,976,368 B2 | 7/2011 | Haucke et al. | |
| 8,025,000 B2 | 9/2011 | Kim et al. | |
| 8,096,860 B2* | 1/2012 | Bolte | A22C 17/002 452/157 |
| 8,147,299 B2* | 4/2012 | McKenna | A22B 5/007 452/155 |
| 8,166,856 B2 | 5/2012 | Kim et al. | |
| 8,688,267 B2 | 4/2014 | Blaine et al. | |
| 8,721,405 B2 | 5/2014 | McKenna et al. | |
| 8,753,177 B2 | 6/2014 | Schroder et al. | |
| 8,758,099 B2* | 6/2014 | Reifenhaeuser | A22C 17/002 452/157 |
| 8,986,080 B2* | 3/2015 | Black | A22B 5/166 452/150 |
| 9,039,498 B2* | 5/2015 | Schwarz | A22C 25/08 452/127 |
| 9,095,146 B2 | 8/2015 | Sigurdsson et al. | |
| 2010/0029187 A1 | 2/2010 | Haucke et al. | |

FOREIGN PATENT DOCUMENTS

| | | |
|---|---|---|
| GB | 2309078 A | 7/1997 |
| WO | 9947885 | 9/1999 |
| WO | 0243502 A2 | 6/2002 |
| WO | 2005090964 A1 | 9/2005 |

OTHER PUBLICATIONS

Danish Search Report; Application No. PA 2011 00607; Date of Completion of Search: Mar. 6, 2012.

* cited by examiner

MEAT INSPECTION SYSTEM

CROSS-REFERENCES TO RELATED APPLICATIONS

This application is a continuation of U.S. patent application Ser. No. 14/799,707 filed on Jul. 15, 2015, incorporated herein by reference, which is a continuation of U.S. Pat. No. 9,095,146 issued on Aug. 4, 2015 (U.S. patent application Ser. No. 14/233,955 filed on Jan. 21, 2014), incorporated herein by reference, which is the national phase application of International Application No. PCT/EP2012/003456 filed on Aug. 13, 2012, incorporated herein by reference, which claims the benefit of priority to Danish Patent Application No, PA 2011 00607 filed on Aug. 12, 2011, incorporated herein by reference, and U.S. Patent Application No. 61/522,867 filed on Aug. 12, 2011, incorporated herein by reference.

FIELD OF THE INVENTION

The invention relates to a system for inspection of meat and parts of meat in order to detect any undesired objects that may be comprised in the meat parts or in between the meat parts. The system comprises supply means for the meat parts and a radiation inspection facility, e.g. an X-ray radiation inspection facility for detecting any undesired objects. Further, the system comprises means for separating meat parts comprising undesired object. Further, the invention relates to a method for performing a meat inspection and sorting.

BACKGROUND OF THE INVENTION

Within the food industry various methods and systems are known for detecting undesired objects in food products and in particular in meat products. As regards meat products it may be of particular relevance to detect bones or bone fragments, for example in connection with meat parts, where a deboning and/or trimming has been performed and where it is desired to ensure that all bones have been removed and/or where it is desired to ensure that fragments of bones have not been left in the meat when performing the deboning process.

In the prior art various methods and systems have been described for detecting e.g. bone or bone fragments in meat parts by means of X-ray detection means and removing meat parts, which comprises detected bone or bone fragments from e.g. a stream of meat parts, for example in order to manually process such meat parts.

An example of such a technique is disclosed in WO 2005/090964 A1, wherein it is described that boneless or deboned meat or fish products are conveyed along a conveyor, wherein the products are formed individually into a shape of substantially uniform thickness while passing an X-ray emitting and sensing means, whereafter image analysis is performed to detect any bone or bone fragments. It is registered which food items or which part of a stream of food items contains bones, bone fragments or other undesired materials and such food items, a whole part of the stream comprising a plurality of food items, many of which do not contain undesired materials, must be removed or routed away in order to ensure that a detected undesired material is removed.

WO 02/43502 A2 relates to an apparatus and a method for detecting and removing undesirable material such as bones, fat, metal, etc. from a workpiece, e.g. a food product. The workpieces are supplied one by one, i.e. separate from each other, by means of a conveyor to a computer-operated X-ray detection apparatus for detecting the position of the individual workpiece and for detecting possible undesirable material and the location of this in each of the workpieces. By means of a cutter a part of the workpiece containing the undesirable materiel is cut off and is later downstream removed manually or by a pickup device. As the workpieces are supplied and conveyed separately one by one and as the detection is performed for each workpiece separately, this will limit the number of workpieces that can be processed per time unit.

It is an object of the invention to provide an improved system and an improved method for inspecting meat for undesired objects and for removing such undesired objects.

In particular, it is an object to provide such a system and such a method, which can perform in a highly automatic manner and whereby an efficient operation and a relatively high flow can be facilitated.

Further, it is an object to minimize the amount of meat that is being removed together with the undesired objects.

It is a particular relevant object of the invention to provide a system and a method for inspecting e.g. a stream or flow of relatively small meat parts, for example trim parts, ground meat, etc. in a quick and effective manner and still be able to ensure that only a minimum of meat parts are removed, when an undesired object is removed.

It is noted that in connection with the present application it will be understood that meat parts comprise meat parts and/or trim parts of animals such as calves, pigs, sheep, etc., and that the meat and meat parts also includes meat from e.g. poultry, fish, etc. Further, it is noted that the meat parts may also be ground meat.

Further, it is noted that the undesired objects, for which the meat parts are inspected in accordance with the present invention, in particular are bones and bone fragments, but that also other objects may be detected, for example metal, glass, plastic, stones, cartilage and other foreign objects. Even further, it is noted that the undesired objects that are detected, may be e.g. fat, meat having particular meat characteristics, e.g. a high fat content, etc. Further meat characteristics that may be detected, are e.g. blood stains, abscess, infections, etc.

In particular, it is a further object of the present invention to present a system and a method, which provides an improved processing speed and efficiency and by means of which the capacity of the radiation detection facility can be used in an optimal manner.

These and other objects are achieved by the invention as explained in further detail in the following.

SUMMARY OF THE INVENTION

The invention relates to a meat inspection and sorting line comprising supply means,
a radiation inspection facility,
a cutting facility and
a reject facility,
wherein meat parts are brought together and fed into the radiation inspection facility by means of a conveyor in a layer of meat parts,
wherein an undesired object is detected by the radiation inspection facility by means of e.g. an X-ray technique,
a part of the layer of meat parts containing the undesired object is identified and separated from the layer of meat parts by the cutting facility, and the identified and separated part of the layer of meat parts containing the undesired object is rejected by the reject facility from the layer of meat parts.

It is noted that in connection with the present application it will be understood that meat parts comprise meat parts and/or trim parts of animals such as calves, pigs, sheep, etc., and that the meat and meat parts also includes meat from e.g. poultry, fish, etc. Further, it is noted that the meat parts may also be ground meat. Even further, it is noted that the meat and meat parts may be of varying sizes, shapes, etc. and that meat parts of different sizes may be processed in accordance with the invention simultaneously, e.g. in the same stream of meat parts.

A layer shall be understood as comprising a plurality of meat parts, wherein at least two of these meat parts are touching each other in an essentially continuous stream of meat parts, wherein, although, gaps or distances may be present in the stream of meat parts.

Hereby, it is achieved that the capacity of the system can be increased, i.e. the amount of meat and/or number of meat parts that is being processed per time unit, when the meat parts are brought together in a layer of meat parts, where the layer is inspected for possible undesired objects, and where a part of the layer containing a detected undesired object is separated from the rest of the layer by the cutting facility and rejected. Since the layer of meat parts is being inspected, a plurality of meat parts comprised in the layer will be inspected simultaneously, which facilitates an increased capacity or operating speed.

Further, in case an undesired object is detected, only a limited part of the layer of meat parts will be removed, since the relevant part, e.g. a transverse slice of the layer of meat parts comprising the undesired object, is being separated by the cutting facility and—after the cutting—can expediently be automatically removed/rejected by the reject facility. Thus, there is no need to remove a relatively long stream of meat parts, only a short piece of which containing an undesired object. According to the invention a cut can e.g. be performed in front of and behind of the position of the undesired object. Thus, it is achieved that only a minimum of meat, e.g. a vertical slice of the layer of meat parts has to be rejected, i.e. the slice comprising the undesired object.

Thus, this constitutes an improved efficiency and an enhanced yield as compared with the prior art, where a whole part of the stream comprising a plurality of meat items are removed, and where a large number of parts will be unnecessarily removed, since the parts tend to stick together and cannot be separated without some difficulty.

Further, an improved efficiency and operating speed, e.g. items pr. minute, is achieved, since e.g. according to a prior art the items or products have to be conveyed, inspected and treated individually, which in particular when a relatively high number of relatively small product items are concerned will be detrimental to the efficiency. When, in accordance with the invention, the meat parts are brought together in a layer comprising a plurality of meat parts, a relatively high throughput can be achieved.

Advantageously, the supply means are configured for supplying meat parts by bringing said meat parts together in an essentially intermingled and/or overlapping manner. Hereby, it is facilitated that a plurality of meat parts are brought together to form a layer to be inspected, in particular a layer, which enables a high capacity and/or an efficient radiation detection to be performed, since the intermingled and/or overlapping meat parts may form a relatively uniform layer, which enables an undesired object to be detected with a high degree of certainty. This is caused by that e.g. the density of the undesired object, e.g. a bone residue, as compared with the different, but otherwise uniform density of the surrounding meat of the meat parts in the layer can be registered by the radiation inspection facility with greater certainty than in case the meat parts are not brought together to form an e.g. uniform layer.

Further, said supply means may advantageously be configured for forming meat parts into a layer of meat parts with said meat parts being in contact with each other and preferably even pressed, whereby voids between the meat parts can be reduced or even avoided, thereby attributing to the uniformity of the layer of meat parts and the uniformity of the density of the meat.

Even further, it is noted that when the meat parts are brought together in a layer, e.g. in an intermingled and/or overlapping form and with the meat parts being in contact with each other, the radiation inspection is performed by radiation propagating through a plurality of meat parts simultaneously, e.g. meat parts located next to each other as well as on top of each other, which enhances the operating efficiency.

It is noted that the X-ray technique of the radiation inspection facility may perform according to e.g. a single energy technique or a dual energy technique, as it will be well-known to a person skilled within the field of radiation technology and in particular X-ray radiation technology. Such technologies are well-described within the prior art and will not be explained in further detail here.

According to a further advantageous embodiment, said undesired object may be a bone or a bone fragment, a piece of cartilage or another object such as a piece of metal, glass, plastic, stone or other foreign objects.

Furthermore, said undesired object may be e.g. fat, meat having particular meat characteristics, e.g. a high fat content, etc. Further meat characteristics that may be detected, are e.g. blood stains, abscess, infections, etc.

According to an advantageous embodiment, the supply means may be designed for feeding the meat parts into the radiation inspection facility in said layer of meat parts, wherein said layer is in the form of an essentially continuous layer having an essentially even thickness.

Hereby, further advantages are achieved, including that the capacity of the radiation detection facility can be used to the full or essentially to the full since a maximum amount of meat parts can be processed by the facility owing to that the layer of meat parts corresponds to the detection field, i.e. the field covered by the detection. Furthermore, it can be achieved that the meat parts can be compressed when forming the layer, e.g. by pressing the meat parts closer together and minimizing void spaces, thereby also increasing the capacity and the efficiency. The layer of meat parts may be formed into an essentially continuous layer having an essentially even thickness by various means, as it will be apparent to a skilled person, for example also by means of e.g. a funnel-shaped arrangement, through which the meat parts are pushed, etc.

Furthermore, it is emphasized that the supply means may preferably also comprise shaping means for shaping the layer of meat in the transverse direction, e.g. by means of side guides or the like, by means of e.g. a funnel-shaped arrangement, through which the meat parts are pushed, etc.

Further, when using a uniform layer of meat parts, it may be achieved that a single energy X-ray technique may be used, while still providing an optimal result.

According to a further advantageous embodiment, said cutting facility may comprise cutting means, e.g. a rotating cutting knife or blade.

Hereby, a quick and efficient cutting can be performed, using for example a rotating cutting knife, e.g. a sword knife or the like, whereby an efficient cutting of the layer in the essentially transverse direction can be performed. It is noted that when a rotating cutting knife such as a sword knife or the like is used, the conveyor will be divided at the cutting location in order for the knife to pass. It will be understood, though, that other manners and means for performing the cutting may be used, which will be apparent to a skilled person, such e.g. laser cutting, water cutting, or the like.

According to a further preferable embodiment, said cutting facility and/or a conveyor may be designed for creating a distance or an added distance between separated parts.

Hereby, it is achieved that the meat parts, that have been cut, will not stick to each other after the cutting. Thus, the cutting will result in relatively sharp cutting surfaces and a clear separation. Furthermore, by creating a distance or gap, the subsequent process of rejecting a separated part can be facilitated, i.e. since it is easier to reject a separated part and since the risk of interfering with the main layer of meat parts is reduced considerably. Thus, hereby the processing or handling speed can also be increased.

It will be understood that a distance or gap between parts of the layer of meat parts, when a cutting has been performed, can be created in various manners and using various means, which will be apparent to a skilled person within e.g. the conveying field. For example can a conveyor downstream of the cutting location be temporarily speeded up subsequent to the cutting and/or a conveyor upstream of the cutting location can temporarily slowed down subsequent to the cutting, such that the two parts of the layer, that have be separated by the cut, will be removed relatively from each other.

According to a still further advantageous embodiment, said reject facility may comprise rejecting means for controllably rejecting a separated part of the layer of meat parts containing an undesired object.

Hereby, the separated parts can be rejected in an efficient manner.

Advantageously, said rejecting means may comprise one or more of
a slidable conveyor or conveyor part,
a pivotable conveyor or conveyor part,
a rejector or
a gripper, a picker or the like.

Thus, it will be understood that various means may be used for rejecting a separated part and that in general it will be understood that when in connection with the present invention a separated part is rejected, it will be e.g. removed, dropped, lifted and moved, picked and moved, gripped, etc. and generally removed from the stream or layer of meat parts. Thus, it will also be understood that e.g. a robot, a gripper, a picker or the like may be used in connection with the reject facility for controllably rejecting a separated part, According to a particular advantageous embodiment, said meat inspection and sorting line may comprise control means for controlling said cutting facility and/or said reject facility on the basis of input from said radiation inspection facility.

Hereby, the operating of the meat inspection and sorting line can be performed in an efficient manner, including that the control means can operate the facilities while keeping track of the detected undesired objects, the separated parts, etc., thereby enhancing the optimal processing and handling. Furthermore, it is emphasized that the control means may also control such operations as speed control of conveyors, including the accelerating and subsequent deceleration in order to achieve gaps between separated parts, etc., while still keeping close track of these, etc.

According to a further advantageous embodiment, said reject facility may be configured for rejecting separated parts to two or more reject tubs, bins or the like or to two or more different reject stations.

Such embodiments may for example be used also for removing e.g. fat or similar meat products from a stream in applications, where a relatively lean yield is required or desired, and where thus a meat part having a high degree of fat content may be labeled as an undesired object. Thus, separated parts containing undesired objects such as bones, bone residues, etc. may be rejected to one reject bin or reject station, while other separated parts containing e.g. a high fat content, may be rejected to another reject bin or reject station, from where the separated parts can be led to e.g. a gate on a grader, where batches of meat are being produced, and where the high fat content parts can be used in achieving a desired fat/lean ratio of the produced batches. Similarly, it will be understood that instead or additionally, parts can be detected by the invention, which contains a low fat content, and which may be separated in a similar fashion and led to e.g. a gate on a grader, where batches of meat are being produced, and where the low fat content parts, i.e. lean parts can be used in achieving a desired fat/lean ratio of the produced batches.

The invention also relates to a method of performing a meat inspection and sorting, wherein meat parts are brought together and fed into a radiation inspection facility by means of a conveyor in a layer of meat parts, wherein an undesired object is detected by the radiation inspection facility by means of e.g. an X-ray technique, a part of the layer of meat parts containing the undesired object is identified and separated from the layer of meat parts by a cutting facility, and the identified and separated part of the layer of meat parts containing the undesired object is rejected by a reject facility from the layer of meat parts.

Advantageously, the method may relate to use of a meat inspection and sorting line according to any of the claims.

According to a further embodiment, a separated part of the layer of meat parts containing an undesired object, which has been rejected, may subsequently be processed manually in order to remove said undesired object.

Further, a separated part of the layer of meat parts containing an undesired object, which has been rejected, may subsequently be subjected to a rescanning or re-inspection process, either by recirculation or by sending the separated part through another processing line and that a possible rescanning or re-inspection process may be performed using a layer of meat parts having a reduced thickness and/or using a lower conveyor speed.

Even further, a separated part of the layer of meat parts containing an undesired object, which has been rejected, may subsequently be processed for other purposes, e.g. for other food products, where the contents of detected undesired objects are not critical.

Furthermore, the invention also relates to a computer program comprising instructions for carrying out the steps of the method according to any one of the claims when said computer program is executed on a suitable computer device.

THE FIGURES

Figure 2A:
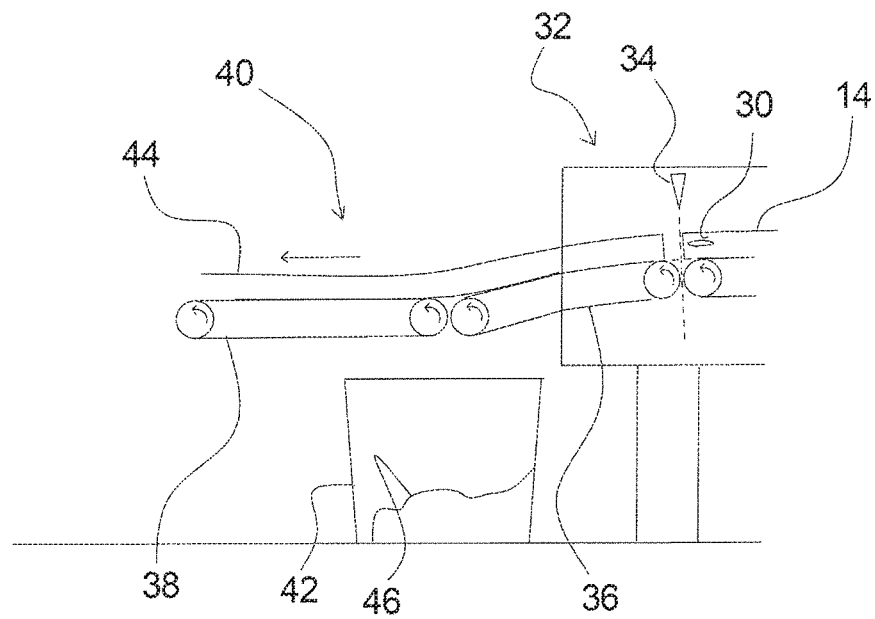
Figure 2B:
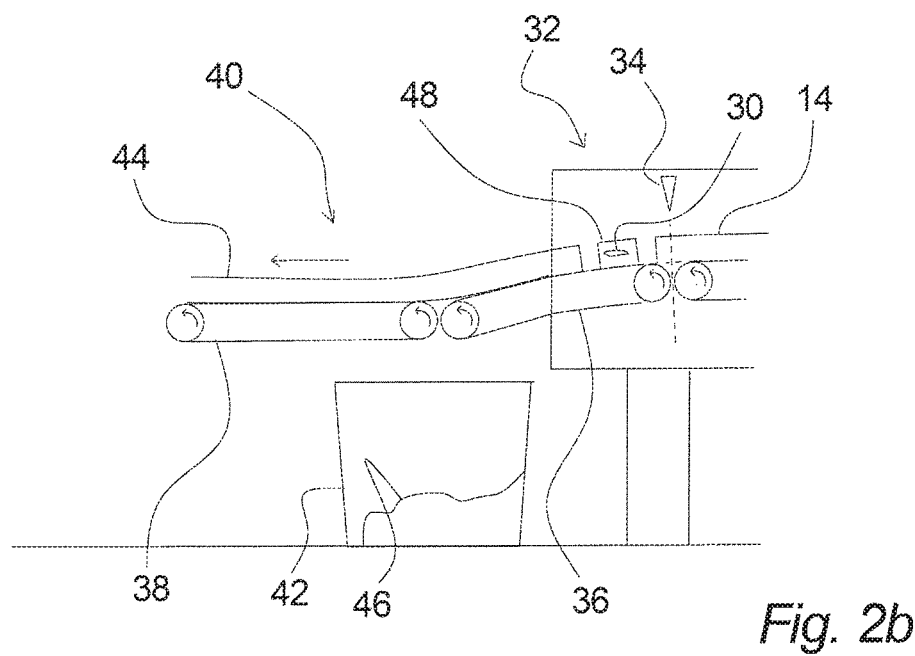
Figure 2C:
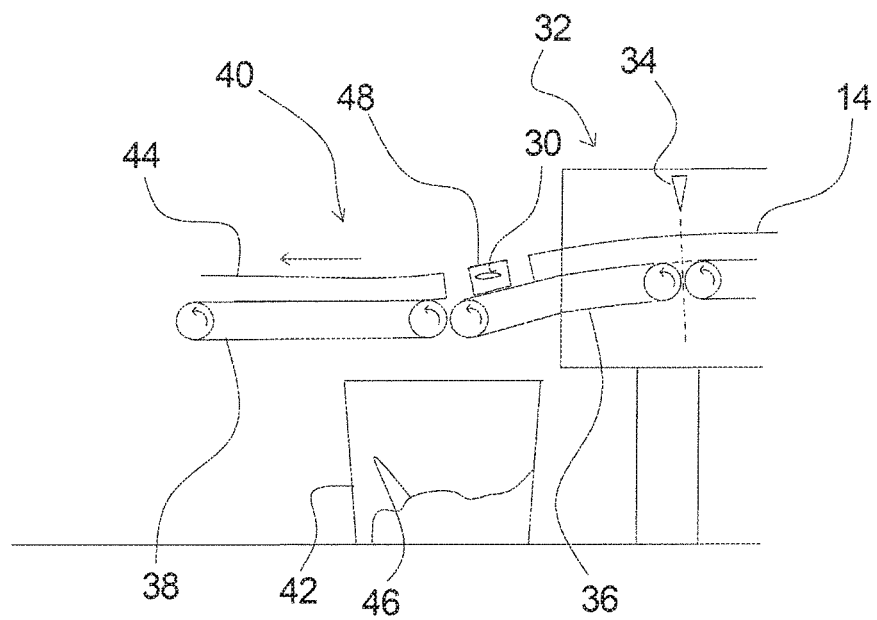
Figure 2D:
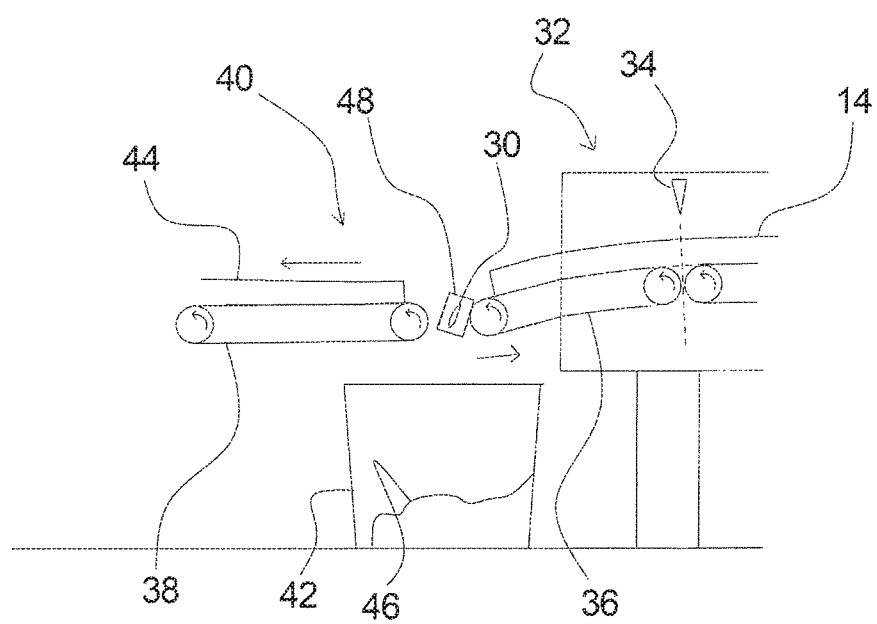
Figure 2E:
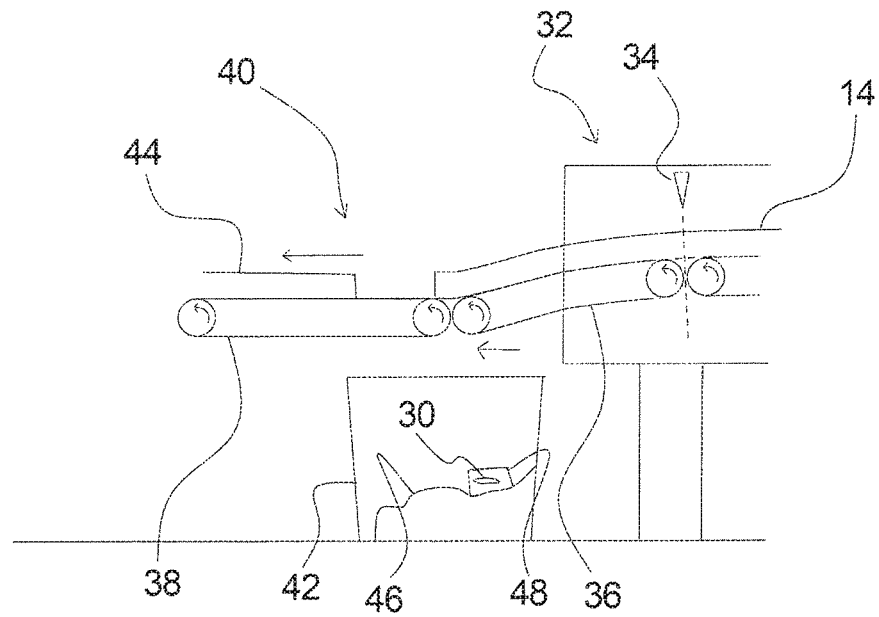
Figure 2F:
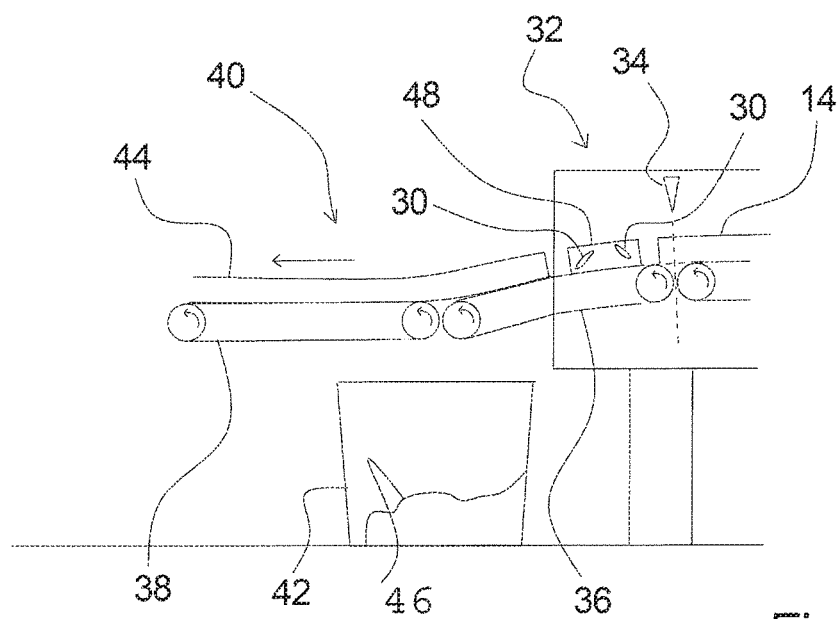
Figure 3A:
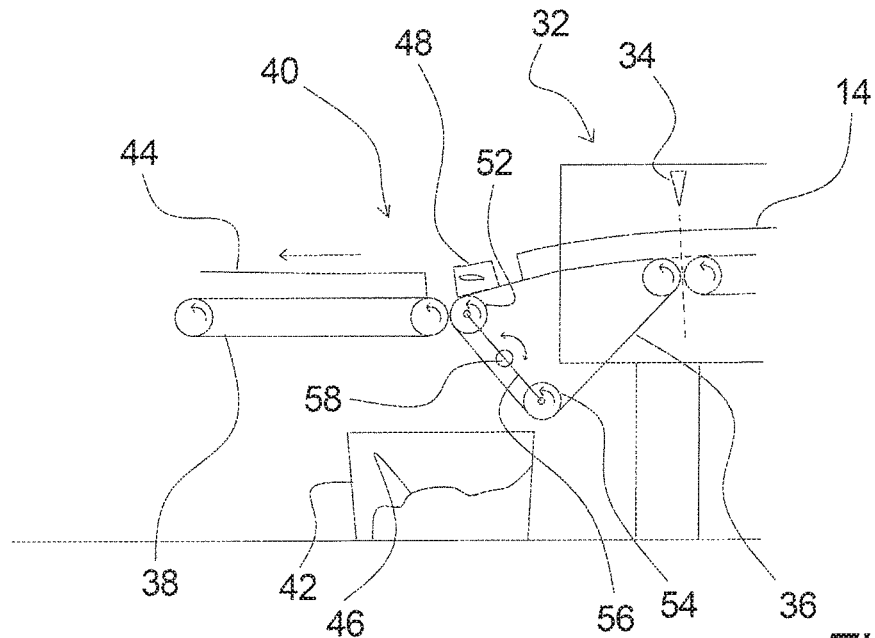
Figure 3B:
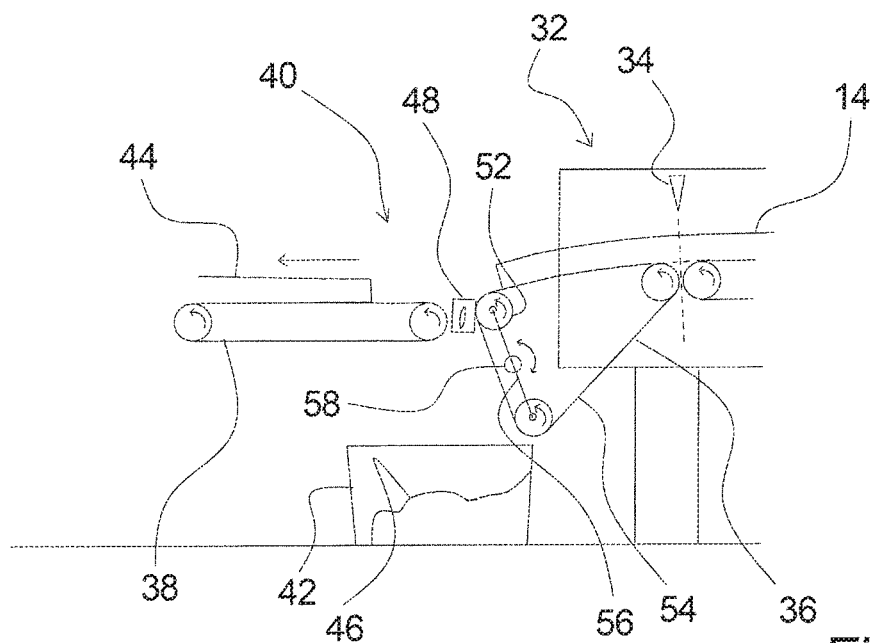
Figure 4:
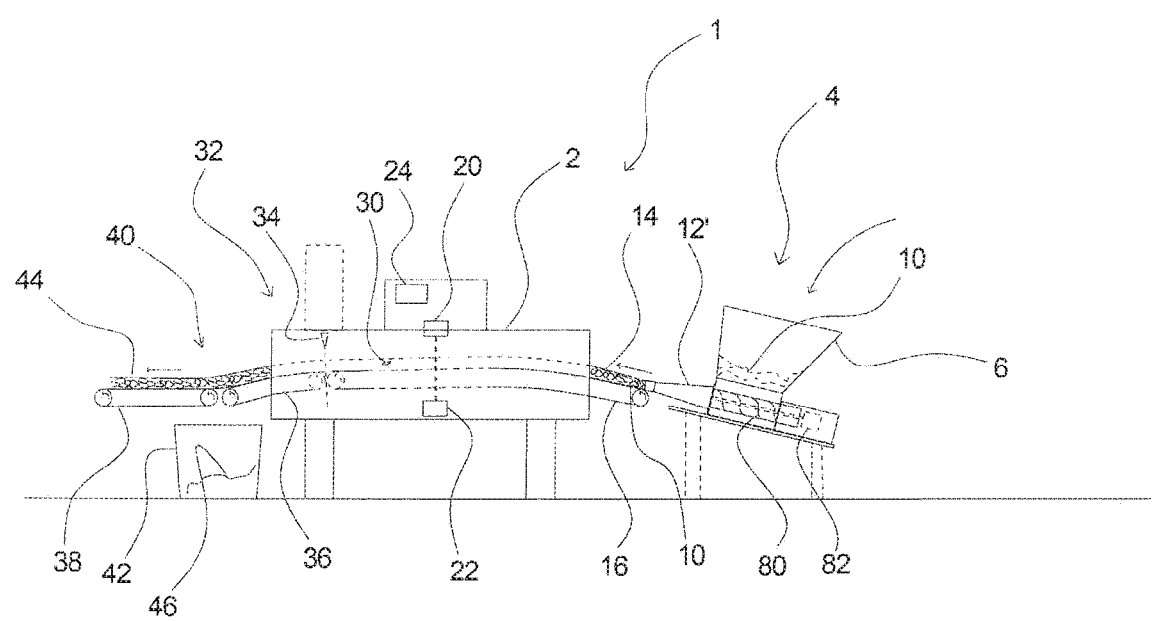

The invention will be explained in further detail below with reference to the figures of which FIG. 1 shows an exemplary embodiment of a meat inspection and sorting line or system, e.g. an X-ray inspection and sorting line, according to the invention in a schematic manner, FIGS. 2a-e show part of the cutting facility and the reject facility in a schematic view, wherein a sequence of steps are shown leading to the separation of a part and rejection of the separated part, FIG. 2f shows a view corresponding to FIG. 2a, but wherein it is illustrated that a separated part may contain more than one undesired object, FIGS. 3a-b show a particular embodiment of the reject facility in a schematic view, and FIG. 4 shows an exemplary embodiment of a meat inspection and sorting line or system, corresponding to FIG. 1 and in a schematic manner, wherein an embodiment of the supply and shaping means are illustrated.

DETAILED DESCRIPTION

An embodiment of a meat inspection and sorting line or system 1, e.g. an X-ray inspection and sorting line, according to the invention is shown in FIG. 1 in a schematic manner, which embodiment will be described in the following.

The system 1 comprises a radiation inspection facility 2, e.g. in particular an X-ray inspection facility, which is shown in a schematic manner in FIG. 1. Further, supply means 4 for supplying meat parts, e.g. pieces of meat, trim parts, ground meat or the like, to be inspected to the radiation inspection facility 2 is shown. The supply means 4 may comprise a receiving chute or the like 6, into which the meat parts to be inspected are delivered as indicated by the arrow. The supply means 4 may preferably be designed to deliver meat parts 10 to a supply conveyor 8, e.g. via an opening at the bottom and at one side of the receiving chute or the like 6. Furthermore, as shown in FIG. 1, meat layer shaping means 12 may be arranged for shaping the delivered meat parts 10 into an essentially continuous layer having an essentially even thickness. These meat layer shaping means 12 may as shown be in the form of an inclining conveyor belt or the like, which serves to even out the meat parts and furthermore serves to compress the meat parts 10 into a substantially uniform layer 14. Other means may be used as well, as it will be exemplified later on in connection with FIG. 4. Furthermore, it will be understood that the supply means 4 may preferably comprise means for shaping the stream of meat parts also in the transverse direction, e.g. guide plates or the like (not shown in FIG. 1), thereby resulting in that the meat parts 10 are shaped into a layer or stream of meat parts 14 having an essentially uniform rectangular sectional shape, which corresponds to the working capability of the radiation inspection facility 2. Hereby, the capacity of the radiation inspection facility 2 will be used in an optimal manner.

The layer or stream of meat parts 14 are as shown delivered from the supply means 4 to an inspection facility conveyor 16, which feeds the layer or stream of meat parts 14 into the radiation inspection facility 2, wherein the layer or stream of meat parts 14 passes radiation detection means, which may be in particular x-ray inspection and detection means, e.g. comprising an X-ray emitter 20 and an X-ray detector 22, which by means of the propagated X-rays can detect e.g. undesired objects in the layer or stream of meat parts 14. Thus, it will be understood that e.g. undesired object within a meat part as well as an undesired object, which is not within a meat part as such, but located between the meat parts, i.e. in the stream or layer of meat parts, can be detected. This detection arrangement may be designed in a multitude of varieties, as it will be well-known to a skilled person within the field, using e.g. single energy or dual energy systems, using various image detection and/or analysis methods, etc.

As shown in FIG. 1, schematically illustrated control means 24 are comprised in the system, located for example in the radiation inspection facility 2, for e.g. controlling and receiving data from the X-ray emitter 20 and the X-ray detector 22, for analyzing data in order to detect possible undesired objects such as e.g. a bone or bone fragment 30 within the layer or stream of meat parts 14 and furthermore for providing relevant data to a cutting facility 32 and a reject facility 40, which will be described in the following.

When an undesired object 30 has been detected, the e.g. position will be registered and/or it will e.g. be determined by for example the control means 24 when the detected object 30 will reach the cutting facility 32, e.g. the location where a cutting of the layer or stream of meat parts 14 can be performed. Such calculations, determinations, etc. can be performed in numerous manners, for example when the transport speed of the inspection facility conveyor 16 and the distance between the detection location and the cutting location are known, which will be readily apparent to a skilled person.

The cutting facility 32, which may be integrated or combined with the radiation inspection facility 2 as shown, comprises cutting means 34 such as for example a knife or blade, which is illustrated in a schematic manner only in FIG. 1, and which may be rotated to cut through the layer or stream of meat parts 14, e.g. across the stream, as indicated with the dash-line in the figure. In order for the cutting means 34 to cut through the layer or stream of meat parts 14, a gap in the conveyor may be arranged, for example between the end of the inspection facility conveyor 16, which naturally in itself may comprise more than one conveyor, and a subsequent output conveyor 36.

When an undesired object 30 has been detected, the cutting means are controlled to cut through the layer or stream of meat parts 14 immediately before the undesired object 30 reaches the cutting location and preferably as close as possibly, and furthermore the cutting means are controlled to cut through the layer or stream of meat parts 14 immediately after the undesired object 30 has passed the cutting location and preferably as close as possible. It will be understood that hereby a part of the layer or stream of meat parts 14 will be cut free, which part will have a length at least corresponding to the length (dimension in the stream direction) of the undesired object 30 and that the length also will be dependent on practical matters, such as e.g. the conveying speed of the inspection facility conveyor 16 and the cutting speed of the cutting means 34. Furthermore, tolerances have to be taken into consideration, e.g. in order to ensure that the detected undesired object 30 is contained in whole in the part that is cut free and that no part of the detected undesired object 30 is cut by the cutting means 34 and left in the layer or stream of meat parts 14 that has not been cut free. Further, it is noted that if two or more undesired objects 30, e.g. two or more bones or bone fragments, have been detected in close proximity to each other, it may be preferable to cut these free in a single combined part instead of performing several cuts and creating several small parts, which have been cut free. In accordance with embodiments of the invention, the e.g. control means 24 may be designed to perform in such various manners in order to optimize the working efficiency.

It is noted that the speed of e.g. the output conveyor 36 may be temporarily increased after a cut has been performed, whereby it is achieved that a distance is created between the two parts and a secure separation of the parts has been achieved, e.g. without the cut parts sticking to each other. Alternatively or additionally, the speed of the inspection facility conveyor 16 may be temporarily reduced after a cut has been performed, whereby it also is achieved that a distance is created.

Subsequent to the cutting facility 32 a reject facility 40 is arranged for rejecting the cut or separated parts of the layer or stream of meat parts 14 containing undesired objects 30. This reject facility 40 comprises a transfer of the layer or stream of meat parts 14 to a reject facility conveyor 38. At the transfer location the separated parts containing undesired objects, which separated parts as described above may be arranged with a distance to the main layer or stream of meat parts 14, can be transferred to e.g. a reject tub, bin or the like 42, which can be placed e.g. underneath the transfer location for accumulating the rejected meat parts 46 containing undesired objects. The separated parts can be rejected in various manners, which will be described later in greater detail, by e.g. sliding the reject facility conveyor 38 or part of this in the conveying direction, thereby creating a gap, when a separated part reaches the location, whereby it will fall into the reject tub, bin or the like 42. Instead, the reject facility conveyor 38 or part of this may be designed to pivot in order to create the gap. Further, various rejector means may be used, e.g. for pushing the separated parts sideways off the conveyor. Other manners of rejecting the parts containing undesired objects may be used, e.g. using for example a robot, a gripper, etc., which will be apparent to a skilled person within the art.

The main layer or stream of meat parts 14, i.e. the parts not comprising undesired objects, or in other word the inspected meat layer 44 with any undesired objects removed will be forwarded for further processing, handling, etc. via the reject facility conveyor 38 and possible further conveyors (not shown), while the rejected meat parts 46 containing undesired objects will be accumulated in the reject tub, bin or the like 42. From the reject tub, bin or the like 42 they can be removed for a subsequent inspection, e.g. manually in order to search for and remove the undesired objects, or alternatively by running the meat through the inspection line again e.g. in order to minimize the amount of meat that has to be manually inspected and searched in order to find and remove the undesired objects.

In FIGS. 2a to 2e are shown part of the cutting facility 32 and the reject facility 40 in an enhanced schematic view, wherein a sequence of steps are shown leading to the separation of a part 48 containing an undesired object 30 and rejection of the separated part 48. In FIG. 2a it is shown that an undesired object 30, which has been detected by the inspection facility 2, is reaching the cutting location and a cut has been performed through the layer 14 of meat parts by the cutting means 34, e.g. a rotating cutting knife or blade, in front of the identified undesired object 30. Furthermore, the output conveyor 36 has been briefly accelerated and decelerated again in order to create a gap or distance between the parts that have been cut, e.g. in order to achieve that the parts do not stick together and in order to achieve that it will be easier later on to reject a part that has been separated. It is noted that since the output conveyor 36 has just been accelerated for a brief period, leading only to a short change in distance, the layer of meat parts in the transport direction may be compressed to take up this distance. It may also be considered to accelerate the one or more further conveyors in the transport direction to compensate for the change.

As mentioned above, a gap or distance may alternatively or additionally be created by temporarily reducing the speed of the inspection facility conveyor 16 after a cut has been performed.

In FIG. 2b it is similarly shown that in a following step the undesired object 30 has been further advanced, a cut has been performed through the layer 14 of meat parts behind the identified undesired object 30, and further the output conveyor 36 has again been briefly accelerated and decelerated in order to create a gap or distance between the parts that have been cut. It will thus be seen that a part 48 has now been cut free and separated from the main stream or layer of meat parts.

In FIG. 2c it is shown that the parts have now been further advanced, while the system, e.g. the control means 24 keeps track of the relevant parts, and that the separated part 48 is now reaching the transfer from the output conveyor 36 to the reject facility 40, e.g. the reject facility conveyor 38.

At this point in time, a gap may be established between these two conveyors by for example arranging the end of the output conveyor 36 to be moved opposite the transport direction as shown in FIG. 2d, whereby the separated part 48 will be allowed to drop into the reject tub or bin 42 to be accumulated with previous rejected parts 46. Instead, it may be preferred to arrange the first end in the transport direction of the reject facility conveyor 38 to be moved in the transport direction, whereby likewise a gap can be created.

After this, as shown in the next step in FIG. 2e, the end of the output conveyor 36, or alternatively the first end in the transport direction of the reject facility conveyor 38, will be returned to its initial position, whereafter normal transport of the layer 14 of meat parts are resumed onto the reject facility conveyor 38.

It will be apparent that the gap between the two conveyors 36 and 38 can be provided in various manners, e.g. as explained by having one end of the output conveyor 36 or one end of the reject facility conveyor 38 being movable in the transport direction, which may be arranged in numerous manners. It will also be apparent that part of the conveyor(s) may be pivotable, whereby a gap can also be established in order to reject a separated part 48. Further, it is apparent that the output conveyor 36 as well as the reject facility conveyor 38 may be configured to achieve a rejection facility and that any combinations of the above examples may be used. Even further, it will be apparent to a skilled person that other means may be used for rejecting a separated part, e.g. a separator for pushing a separated part sideways off the conveyor(s) or similar separator means, or a robot, a gripper, etc.

In FIG. 2f, which in essence corresponds to the step shown in FIG. 2b, it is shown that in case two or more undesired objects 30 are positioned close to each other, it may be preferable to include these in a single separated part 48 instead of cutting smaller parts. This may be the case, when it is not possible to cut between the two or more objects, when it is not in reality, e.g. due to cutting speed/time vs. transport speed, practically to cut between the two or more objects and when it is simply more efficient to have only a single separated part, which have to be handled by e.g. the reject facility 40, instead of a plurality of smaller separated parts 48.

In FIGS. 3a and 3b is shown a particular embodiment of the reject facility 40 in a schematic view, wherein it is shown how the output conveyor 36 may be configured for providing a gap between the two conveyors 36 and 38. As shown in FIG. 3a, the conveyor 36 comprises at least three rollers, of which two, i.e. the roller 52 and the roller 54, are supported by a frame 56, which is pivotable in relation to an axis 58. In the position shown in FIG. 3a, the meat parts are transferred to the reject facility conveyor 38, but when a separated part 48 reaches the transfer location, the frame 56 may be pivoted to the position shown in FIG. 3b, whereby the roller 52 will be moved opposite the transport direction and the separated part 48 will quickly drop downwards, whereafter the frame 56 may be returned to its initial position. As it will be understood, this embodiment has the particular advantage that the conveyor 36, aided by the transport speed, will quickly disappear from under the separated part 48, which will thus be quickly dropped down into the reject tub or bin 42. Thus, the drop or reject time will not depend entirely on the conveyor speed and may thus be preferable to an embodiment, where the gap is created by moving the first end of the reject facility conveyor 38 in the transport direction.

In FIG. 4 a further embodiment is illustrated. FIG. 4 shows an exemplary embodiment of a meat inspection and sorting line or system, corresponding to FIG. 1 and in a schematic manner, but wherein an embodiment of the supply means 4 and meat layer shaping means 12' are illustrated. A receiving chute 6 or the like is provided as shown in connection with FIG. 1 for receiving meat parts 10 from any suitable means. At the bottom of the receiving chute 6 a screw conveyor 80 may be provided, driven by e.g. an electric motor 82 or any other suitable driving means. Thus, the meat parts 10 are conveyed, e.g. pushed towards the radiation inspection facility 2 via meat layer shaping means 12', which in the illustrated example is a funnel shaped arrangement, placed with its wider end at the outlet of the screw conveyor 80 and with its smaller end at the inlet of the radiation inspection facility 2, e.g. at the supply end of the inspection facility conveyor 16. Thus, the meat parts 10 are in this manner compressed or squeezed together by the funnel shape, thereby reducing the air volume, e.g. caused by gaps between the meat parts, in the resulting layer of meat parts. The outlet end of the meat layer shaping means 12', i.e. the smaller end, will define the shape of the layer of meat parts 14 and may preferably be of a rectangular shape.

As mentioned above, other embodiments are possible, including any combinations of such embodiments and the embodiments disclosed above and shown in the figures.

Further, it is noted that the meat inspection and sorting line or system according to the invention and its use has been described above with reference to particular embodiments, but it will be understood that the invention is not limited to the particular examples described above and shown in the drawings, but may be modified in numerous manners within the scope of the invention as specified in the claims.

LIST OF REFERENCES

1 Meat inspection and sorting line
2 Radiation inspection facility
4 Supply means
6 Receiving chute or the like
8 Supply conveyor
10 Meat parts
12, 12' Meat layer shaping means
14 Layer of meat parts, un-inspected
16 Inspection facility conveyor
20 X-ray emitter
22 X-ray detector
24 Control means
30 Undesired object, e.g. a bone, bone fragments, piece of foreign object
32 Cutting facility
34 Cutting means, e.g. a knife or blade
36 Output conveyor
38 Reject facility conveyor
40 Reject facility
42 Reject tub, bin or the like
44 Inspected meat layer with undesired objects removed
46 Rejected meat parts containing undesired objects
48 Separated part
52, 54 Rollers
56 Support frame
58 Axis
80 Screw conveyor
82 Drive means, e.g. electric motor

The invention claimed is:

1. A method of performing a meat inspection and sorting, comprising the steps of:
bringing meat parts together in a stream of intermingled and/or overlapping meat parts for feeding into a radiation inspection facility, wherein an undesired object located in the stream of intermingled and/or overlapping meat parts is detected by the radiation inspection facility;
identifying a part of the stream of intermingled and/or overlapping meat parts containing the undesired object for separation from the stream of meat parts at a cutting facility;
separating, via the cutting facility, said part containing the undesired object from the stream of intermingled and/or overlapping meat parts;
and
rejecting the separated part of the stream of intermingled and/or overlapping meat parts containing the undesired object at a reject facility.

2. The method according to claim 1, wherein the method is performed using a meat inspection and sorting line that comprises:
a supply source;
a radiation inspection facility including a radiation device;
a cutting facility; and
a reject facility;
wherein the step of bringing meat parts together in a stream of intermingled and/or overlapping meat parts comprising small meat parts or ground meat is performed by the supply source, and wherein the supply source further feeds said meat parts into the radiation inspection facility, and wherein
the step of detecting an undesired object is performed by the radiation inspection facility by the radiation device, and wherein
the step of identifying and separating said part of the stream of meat parts containing the undesired object from the stream of meat parts is performed by the cutting facility, and wherein
the step of rejecting said identified and separated part of the stream containing the undesired object from the stream of meat parts is performed by the reject facility.

3. The method according to claim 1, wherein a separated part of the stream of intermingled and/or overlapping meat parts containing an undesired object, which has been rejected, is subsequently processed manually in order to remove said undesired object.

4. The method according to claim 1, wherein a separated part of the stream of intermingled and/or overlapping meat parts stream containing an undesired object, which has been rejected, is subsequently subjected to a rescanning or re-inspection process, either by recirculation or by sending the separated part through another processing line and that a possible rescanning or re-inspection process may be performed using a stream of meat parts having a reduced thickness and/or using a lower stream speed.

5. The method according to claim 1, wherein a separated part of the stream of intermingled and/or overlapping meat parts containing an undesired object, which have been rejected, is subsequently processed for other purposes, e.g. for other food products, where the contents of detected undesired objects are not critical.

6. A computer program comprising instructions for carrying out the steps of the method according to claim 1 when said computer program is executed on a suitable computer device.

7. The method according to claim 1, wherein said stream of intermingled and/or overlapping meat parts is in the form of a layer of meat parts.

8. The method according to claim 1, wherein the step of bringing meat parts together in a stream of meat parts for feeding into a radiation inspection facility comprises using a conveyor.

9. The method according to claim 1, wherein the meat parts brought together in a stream of meat parts are comprised of small pieces of meat.

10. The method according to claim 1, wherein the meat parts brought together in a stream of meat parts are comprised of ground meat.

11. The method according to claim 1, wherein the stream of intermingled and/or overlapping meat parts is fed into a radiation inspection facility as a stream of meat parts formed into a shape of substantially uniform thickness.

12. A method of performing a meat inspection and sorting, comprising the steps of:
bringing meat parts together in a stream of intermingled and/or overlapping meat parts comprised of small pieces of meat or ground meat for feeding into a radiation inspection facility, wherein an undesired object is detected by the radiation inspection facility;
identifying a part of the stream of intermingled and/or overlapping meat parts containing the undesired object for separation from the stream of intermingled and/or overlapping meat parts at a cutting facility; and
rejecting the separated part of the stream of intermingled and/or overlapping meat parts containing the undesired object at a reject facility.

13. The method according to claim 12, wherein the method is performed using a meat inspection and sorting line that comprises:
a supply source;
a radiation inspection facility including a radiation device;
a cutting facility; and
a reject facility;
wherein the step of bringing meat parts together in the stream of intermingled and/or overlapping meat parts is performed by the supply source, and wherein the supply source further feeds said meat parts into the radiation inspection facility, and wherein the step of detecting an undesired object is performed by the radiation inspection facility by the radiation device, and wherein the step of identifying and separating said part of the stream of meat parts containing the undesired object from the stream of meat parts is performed by the cutting facility, and wherein the step of rejecting said identified and separated part of the stream containing the undesired object from the stream of meat parts is performed by the reject facility.

14. The method according to claim 12, wherein a separated part of the stream of intermingled and/or overlapping meat parts containing an undesired object, which has been rejected, is subsequently processed manually in order to remove said undesired object.

15. The method according to claim 12, wherein a separated part of the stream of intermingled and/or overlapping meat parts containing an undesired object, which has been rejected, is subsequently subjected to a rescanning or re-inspection process, either by recirculation or by sending the separated part through another processing line and that a possible rescanning or re-inspection process may be performed using a stream of meat parts having a reduced thickness and/or using a lower stream speed.

16. The method according to claim 12, wherein a separated part of the stream of intermingled and/or overlapping meat parts containing an undesired object, which have been rejected, is subsequently processed for other purposes where the contents of detected undesired objects are not critical.

17. A computer program comprising instructions for carrying out the steps of the method according to claim 12 when said computer program is executed on a suitable computer device.

18. The method according to claim 12, wherein said stream of intermingled and/or overlapping meat parts is in the form of a layer of meat parts.

19. The method according to claim 12, wherein the step of bringing meat parts together in a stream of meat parts for feeding into a radiation inspection facility comprises using a conveyor.

20. The method according to claim 12, wherein the stream of intermingled and/or overlapping meat parts is fed into a radiation inspection facility as a stream of meat parts formed into a shape of substantially uniform thickness.

21. A method of performing a meat inspection and sorting, comprising the steps of:
bringing meat parts together in a stream of intermingled and/or overlapping meat parts comprised of ground meat formed into a shape of substantially uniform thickness for feeding into a radiation inspection facility, wherein an undesired object is detected by the radiation inspection facility by means of a radiation technique;
identifying a part of the stream of meat parts containing the undesired object for separation from the stream of meat parts at a cutting facility; and
rejecting the separated part of the stream of meat parts containing the undesired object at a reject facility.

* * * * *